United States Patent
Rudigier-Voigt et al.

(10) Patent No.: US 12,091,358 B2
(45) Date of Patent: Sep. 17, 2024

(54) GLASS CYLINDER FOR A PISTON-CYLINDER ASSEMBLY WITH REDUCED FRICTION, AND METHOD FOR TREATING A GLASS CYLINDER FOR A PISTON-CYLINDER ASSEMBLY

(71) Applicants: SCHOTT Pharma AG & Co. KGaA, Mainz (DE); SCHOTT Pharma Schweiz AG, St. Gallen (CH)

(72) Inventors: Eveline Rudigier-Voigt, Mainz (DE); Jovanna Djordjevic-Reiss, Mainz (DE); Thorsten Schneider, Nackenheim (DE); Joerg Geiger, Gais (CH); Daniel Grigas, Büdingen (DE)

(73) Assignees: SCHOTT Pharma AG & Co., KGaA, Mainz (DE); SCHOTT Pharma Schweiz AG, St. Galien (CN)

( * ) Notice: Subject to any disclaimer, the term of this patent is extended or adjusted under 35 U.S.C. 154(b) by 859 days.

(21) Appl. No.: 16/732,737

(22) Filed: Jan. 2, 2020

(65) Prior Publication Data
US 2020/0140330 A1 May 7, 2020

Related U.S. Application Data

(63) Continuation of application No. PCT/EP2018/067754, filed on Jul. 2, 2018.

(30) Foreign Application Priority Data
Jul. 5, 2017 (DE) .................... 10 2017 114 959.7

(51) Int. Cl.
*A61M 5/31* (2006.01)
*C03C 23/00* (2006.01)

(52) U.S. Cl.
CPC ......... *C03C 23/004* (2013.01); *A61M 5/3129* (2013.01); *C03C 23/002* (2013.01);
(Continued)

(58) Field of Classification Search
CPC ...... A61M 2005/3131; A61M 2207/00; A61M 5/3129; C03C 23/004; C03C 23/002; C03C 23/006
See application file for complete search history.

(56) References Cited

U.S. PATENT DOCUMENTS

| 4,767,414 A | 8/1988 | Williams et al. |
| 8,747,962 B2 | 6/2014 | Bicker et al. |

(Continued)

FOREIGN PATENT DOCUMENTS

| JP | 10-24105 A | 1/1998 |
| JP | 2006-49849 A | 2/2006 |

(Continued)

OTHER PUBLICATIONS

Chinese Office Action dated Sep. 1, 2021 for Chinese Application Serial No. 201880045323.9 (9 pages).

(Continued)

*Primary Examiner* — Lauren P Farrar
(74) *Attorney, Agent, or Firm* — Taylor IP, P.C.

(57) ABSTRACT

A method of treating a glass cylinder for a piston-cylinder arrangement for reducing the friction of a piston on an inner cylinder wall of the glass cylinder includes: elevating surface energy of glass of an interior bounded by the inner cylinder wall and hence lowering a contact angle of the glass with water. The contact angle is lowered by: a gas discharge that acts on the glass at the inner cylinder wall and is generated by an electric or electromagnetic field; or the action of ozone on the glass surface. The glass with the (Continued)

lowered contact angle is contacted with water to form a water film on the contacted glass.

18 Claims, 5 Drawing Sheets

(52) U.S. Cl.
CPC ... *C03C 23/006* (2013.01); *A61M 2005/3131* (2013.01); *A61M 2207/00* (2013.01)

(56) References Cited

U.S. PATENT DOCUMENTS

| | | | |
|---|---|---|---|
| 9,623,411 B1* | 4/2017 | Frenzel | B01F 31/651 |
| 2003/0023206 A1* | 1/2003 | Bausmith, III | A61M 5/007 |
| | | | 604/218 |
| 2004/0231926 A1* | 11/2004 | Sakhrani | C10M 107/50 |
| | | | 184/18 |
| 2005/0137533 A1* | 6/2005 | Sudo | A61M 5/31511 |
| | | | 604/218 |
| 2008/0044588 A1 | 2/2008 | Sakhrani | |
| 2008/0071228 A1 | 3/2008 | Wu et al. | |
| 2012/0251748 A1* | 10/2012 | Ashmead | A61M 5/31513 |
| | | | 428/34.7 |
| 2012/0277686 A1 | 11/2012 | Muramatsu | |
| 2013/0171334 A1 | 7/2013 | Bruna et al. | |
| 2014/0273249 A1* | 9/2014 | Yuan | G01N 33/86 |
| | | | 427/337 |
| 2016/0052821 A1* | 2/2016 | Busardo | C23C 14/5853 |
| | | | 501/70 |
| 2018/0243508 A1 | 8/2018 | Berg et al. | |
| 2019/0093226 A1* | 3/2019 | Newton | C23C 16/45563 |

FOREIGN PATENT DOCUMENTS

| | | |
|---|---|---|
| WO | 98/17339 A1 | 4/1998 |
| WO | 2011/029628 A1 | 3/2011 |
| WO | 2012/034648 A1 | 3/2012 |
| WO | 2012/097972 A1 | 7/2012 |
| WO | 2018/157097 A1 | 8/2018 |

OTHER PUBLICATIONS

Notice of Submission of the International Search Report and Written Notice to the International Searching Authority or Statement dated Sep. 21, 2018 for International Application No. PCT/EP2018/067754 (6 page).

Written Notice From the International Searching Authority dated Sep. 21, 2018 for International Application No. PCT/EP2018/067754 (8 page).

German Office Action dated Mar. 8, 2018 for German Application No. 10 2017 114 959.7 (10 pages).

"Modification of glass surfaces adhesion properties by atmospheric pressure plasma torch", J. Abenojar et al., International Journal of Adhesion & Adhesives 44, pp. 1-8, 2013 (8 pages).

"Absorption of nitrogen dioxide and nitric oxide by soda lime", T. Ishibe et al., British Journal of Anaesthesia, 75, pp. 330-333, 1995 (4 pages).

"Surface OH group governing wettability of commercial glasses", S. Takeda et al., Journal of Non-Crystalline Solids, 249, pp. 41-46, 1999 (6 pages).

"Plasma Treatment of Glass Surfaces Using Diffuse Coplanar Surface Barrier Discharge in Ambient Air", Tomáš Homola et al., Plasma Chem Plasma Process, 33, pp. 881-894, 2013 (14 pages).

Chinese Office Action dated Apr. 18, 2022 for Chinese Application No. 201880045323.9 (11 pages).

English translation of Chinese Office Action dated Apr. 18, 2022 for Chinese Application No. 201880045323.9 (14 pages).

"Material Science and Engineering Foundation", Cai Xun, Shanghai Jiaotong University Press, Jul. 2010 (2 pages).

English translation of "Material Science and Engineering Foundation", Cai Xun, Shanghai Jiaotong University Press, Jul. 2010 (3 pages).

"Ion Bombardment Percolation Technology", Lieyu Yang et al., People's Transport Press, Mar. 1990 (6 pages).

English translation of "Ion Bombardment Percolation Technology", Lieyu Yang et al., People's Transport Press, Mar. 1990 (9 pages).

"Study of the Application of Gas Discharge in Industry", Wang Changquan, Shandong University Press, Aug. 2014 (4 pages).

English translation of "Study of the Application of Gas Discharge in Industry", Wang Changquan, Shandong University Press, Aug. 2014 (5 pages).

English machine translation of Japanese Patent No. 2006-49849 issued Feb. 16, 2006 (24 pages).

* cited by examiner

GLASS CYLINDER FOR A PISTON-CYLINDER ASSEMBLY WITH REDUCED FRICTION, AND METHOD FOR TREATING A GLASS CYLINDER FOR A PISTON-CYLINDER ASSEMBLY

CROSS REFERENCE TO RELATED APPLICATIONS

This is a continuation of PCT application No. PCT/EP2018/067754, entitled "GLASS CYLINDER FOR A PISTON-CYLINDER ASSEMBLY WITH REDUCED FRICTION, AND METHOD FOR TREATING A GLASS CYLINDER FOR A PISTON-CYLINDER ASSEMBLY", filed Jul. 2, 2018, which is incorporated herein by reference.

BACKGROUND OF THE INVENTION

1. Field of the Invention

The invention relates generally to arrangements with a cylinder and a piston that runs therein. The invention specifically relates to such arrangements with a glass cylinder.

2. Description of the Related Art

Piston-cylinder arrangements are widespread in mechanical engineering. Typically, metal is used here as material both for the piston and for the cylinder. In order to be able to allow the piston to slide within the cylinder in a sealed manner, lubricants are used.

In specific fields of industry, plastics are also used. Some plastics have the benefit of causing only low friction, and so even lubricant-free arrangements are possible. One example of this is plastic syringes for administration of medicaments.

As well as plastic syringes, glass syringes are also used, often also in the form of prefilled syringes. Prefillable syringes offer multiple advantages in pharmaceutical packaging over the conventional combination of vials and disposable syringes, for example exact medicament dosage, assurance of sterility, saving of time in emergency situations, user-friendliness and—not least—less waste and lower environmental pollution. A prefilled syringe is typically defined as a three-part device consisting of components (a) syringe cylinder with a fitted needle or what is called a Luer adapter, (b) rubber stopper that provides or assures vessel seal integrity and (c) a plastic piston rod which is used to move the stopper through the glass cylinder and hence administer the medicament. Prefillable glass syringes are washed, siliconized, sterilized and packaged by the primary packaging manufacturer. Thus, all syringes also contain an invisible fourth component, the lubricant, which is often neglected and can have a great effect on the syringe function and medicament stability.

Glass syringes offer the advantage of high heat resistance, and so they can be sterilized in a simple manner. In addition, permeability to gases is very low, by contrast with plastics. It is therefore possible to store medicaments in the syringe over longer periods as well. On the other hand, glass is a material of brittle hardness where jamming or seizure with breaking-off of glass particles can quickly take place if lubrication is insufficient. It is therefore known that glass syringes can be provided with a friction-reducing coating or a lubricant on the inside. Customarily in the field, lubricity is nowadays assured by a controlled siliconizing process of which the silicone profile can be matched individually to the particular customer demands. Typically, silicone oils are used for the purpose.

Multiple aspects of this syringe siliconization constitute a challenge to their use as prefilled syringes. For instance, in specific cases, even small amounts of unbound silicone oil or silicone particles significantly affect the medicament and hence lower efficacy, which should be avoided particularly in relation to biotech pharmaceuticals since there can be aggregation of specific proteins in this case. For the reasons mentioned (avoidance of silicone particles in medicaments and dispensing completely with silicone for highly sensitive medicaments), it is desirable at least to significantly reduce the silicone content or to dispense with silicone entirely, keeping the same friction properties and container closure integrity.

The siliconization of the primary pharmaceutical packaging medium, more specifically the syringe cylinder, is nowadays an extremely important aspect of the production of sterile, prefillable glass syringes since the functional interaction of the glass body and the stopper is crucial to the efficiency of the overall system. Both inadequate and excessive siliconization can cause problems already described in this connection. Therefore, one trend—by use of modern application technologies—is to achieve an extremely uniform distribution of silicone oil in glass syringes, associated with drastically reduced amounts of silicone oil. A further way of minimizing the amount of free silicone oil in a syringe is the thermal fixing of the silicone oil on the glass surface in a process which is referred to as "baked on silicone". Silicone-oil-free or lubricant-free glass bodies (e.g. syringes or carpules) are of great interest with regard to the disadvantages mentioned and the constantly growing market of highly sensitive biotech pharmaceuticals. Biotech pharmaceuticals are an important class of medicaments (e.g. insulin, vaccines, antibodies, blood products, hormones, cytokines) that are produced with great technological complexity and complex development and manufacturing methods and are very sensitive to lubricants (e.g. silicone oil), resulting in an increase in the demands on conventional syringe technology.

For plastic syringes (COC or COP), the lubricity of specific fluoropolymer coatings on specially developed piston gaskets is already being utilized to make the siliconization of these syringes completely superfluous. However, this approach is only partly applicable to glass surfaces since there is a significant difference in the material properties of plastics and glass. Glass surfaces, compared to plastic surfaces, are subject to higher dynamics or interaction with the surrounding atmosphere in the form of surface reactions. In view of these aspects, specific considerations have to be made for prefilled glass syringe devices and similar devices (e.g. carpules) in order to keep their components sterile and assure the stability thereof and optical clarity with transport and storage for up to a few years. Specifically the friction between gasket material and syringe body can be considerable, with the resultant need to reduce friction between gasket and glass cylinder in a stable manner over the period of storage up to use without the use of oils or other lubricants.

U.S. Pat. No. 4,767,414 A describes a method of reducing the static and dynamic friction between sliding surfaces by applying a lubricant film to at least one of the surfaces. This involves applying a low molecular weight silicone oil to one of the surfaces. The silicone oil and the surface are plasma-treated.

US 2004/0231926 A1 describes a method of producing a lubrication layer in which the lubrication layer is cured at atmospheric pressure using an atmospheric pressure plasma inter alia. As well as silicone oil-based layers, it is also possible to produce perfluoro polyether-based lubricant layers. However, the breakout force, i.e. the sliding friction of the latter layers, is found to be higher compared to cured silicone oil layers. Moreover, in atmospheric pressure treatment, especially atmospheric pressure plasma treatment, there can be elevated introduction of gases, especially also of reaction products of the plasma into the layer.

WO 2011/029628 A1 also discloses implementing a silicone-free sliding layer for a glass syringe with particularly low friction by crosslinking a silicone-free organic fluid in a low-pressure glow discharge.

Use is made of silicone sliding layers in the case of plastic syringes as well. Such sliding layers are known, for example, from US 2012/277686 A1 or US 2008/071228 A1.

At least for particular active ingredients, it would be desirable if it were possible to use a glass syringe without a sliding layer on the glass cylinder that nevertheless has good sliding properties. This would also be advantageous for other piston-cylinder arrangements with glass cylinders.

SUMMARY OF THE INVENTION

Exemplary embodiments disclosed herein provide a glass cylinder with a lowered contact angle with water.

In some exemplary embodiments provided according to the present invention, a method of treating a glass cylinder for a piston-cylinder arrangement for reducing the friction of a piston on an inner cylinder wall of the glass cylinder includes elevating surface energy of glass of an interior bounded by the inner cylinder wall and hence lowering a contact angle of the glass with water. The contact angle is lowered by: a gas discharge that acts on the glass at the inner cylinder wall and is generated by an electric or electromagnetic field; or the action of ozone on the glass surface.

In some exemplary embodiments provided according to the present invention, a glass cylinder for a piston-cylinder arrangement includes an interior bounded by an inner cylinder wall. A surface of the interior of the cylinder is formed by a glass of the glass cylinder and a contact angle of the surface with water is less than 15° so the surface is hydrophilic.

In some exemplary embodiments provided according to the present invention, a piston-cylinder arrangement includes: a glass cylinder having an interior bounded by an inner cylinder wall, a surface of the interior of the cylinder being formed by a glass of the glass cylinder and a contact angle of the surface with water is less than 15° so the surface is hydrophilic; and a piston inserted into the glass cylinder that runs directly on the glass of the glass cylinder. At least a running surface of the piston is formed by a plastic that has a greater contact angle with water than the surface of the inner cylinder wall formed by the glass of the glass cylinder.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
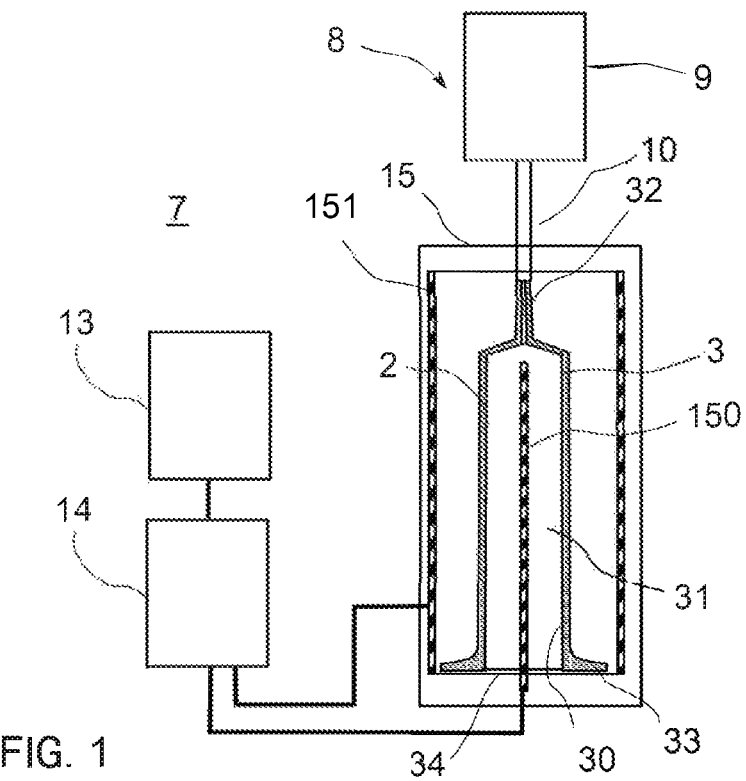
FIG. 1 illustrates an exemplary embodiment of an apparatus provided according to the invention for treating a glass cylinder using corona discharge.

Exemplary embodiments disclosed herein provide a method of treating a glass cylinder for a piston-cylinder arrangement for reducing the friction of the piston on the inner cylinder wall. The surface energy of the glass is elevated in the interior bounded by the inner cylinder wall and hence the contact angle of the glass with water is lowered by a gas discharge that acts on the glass at the inner cylinder wall and is generated by an electric or electromagnetic field, or by the action of ozone on the glass surface.

In some embodiments, after the effect of the gas discharge or of the ozone, the glass is contacted with water on the inside of the cylinder.

In some embodiments, the glass cylinder is a glass syringe.

To achieve a sliding effect that enables simple movement of the piston in the glass cylinder, the coefficient of friction has to date been altered in the direction of large water contact angles. This hydrophobizes the surface of the glass cylinder. The likewise hydrophobic sliding partner, in this case the gasket or plunger, can slide efficiently over the surface with little force. This step is achieved in the prior art, for example, by siliconization of the glass surface.

Exemplary embodiments provided according to the invention take the opposite approach by creating a hydrophilic glass surface. As a result of the wetting properties of the surface, a film of water can form and the gasket slides on this water film with little force.

In some embodiments, the water is not water from an active ingredient formulation accommodated in by the piston-cylinder arrangement. Instead, the loading with water is merely temporary. Typically, the glass cylinder, after the loading with water, is stored intermediately in the empty state until it is filled with the active ingredient formulation to be administered, which is often likewise water-based or at least contains water. In some embodiments, the contacting with water can, however, also be effected by filling with an aqueous active ingredient formulation. Even without temporary loading with water, the surface can also remain stable for a long period with regard to its hydrophilic properties before filling with an active ingredient formulation.

When the increase in the surface energy of the glass is caused by the effect of ozone on the glass surface, the ozone may be produced by at least one of the processes of:
 a gas discharge in an oxygen-containing gas,
 an irradiation with ionizing rays,
 a UV irradiation.

In some embodiments, the gas discharge is effected in an oxygen-containing gas, especially pure oxygen, or a gas mixture, for instance an oxygen-nitrogen mixture or an oxygen-noble gas mixture. It has been found that air is also suitable as process gas to cause the lowering of the contact angle with water in accordance with the invention.

In some embodiments, no low-pressure gas discharge is conducted. Instead, the gas discharge can be effected at a gas pressure of at least 100 millibars. A gas discharge under atmospheric pressure may be used. In this way, there is no need for sealing of the glass cylinder and evacuation. In some embodiments, the gas discharge is effected at low pressure of at most 10 mbar. An exemplary pressure is, for example, 0.3 millibar.

A gas discharge in the form of a corona discharge is suitable. This discharge enables conducting of the treatment under atmospheric pressure as well, and establishment of a homogeneous surface energy on the inside of the glass cylinder. In one variant of corona treatment, it is also possible to use ozone. Ozone can also be generated in a gas discharge, for instance a plasma discharge or by incidence of UV light.

In some embodiments, the gas discharge comprises a plasma treatment, or the generation of a plasma.

The plasma treatment in the context of this invention is referred to as a particular form of gas discharge in which the discharge leads to formation of a plasma. For the plasma treatment, it is possible to use electromagnetic alternating fields for generation of the gas discharge in the form of a plasma. Suitable alternating fields are RF, HF or microwave fields. The term "gas discharge" in the context of this disclosure is generally not limited to discharges in DC voltage fields.

There are various options for the loading with water. For example, the glass cylinder can be rinsed with water or dipped into a water bath. Spraying or ultrasound nebulization are further options. In some embodiments of the method, the loading with water comprises the introducing of water vapor into the interior of the glass cylinder. This offers the advantage that there is no need for a drying step for removal of remaining water after emptying. In addition, the supply of water vapor can avoid contamination of the glass surface with substances dissolved in the water. The water vapor may be supplied in the form of water-enriched air.

After they have been produced and stored under normal atmospheric conditions, glass surfaces, especially after a period of time under air, have a surface energy associated with a contact angle of typically 20° to 60°. This contact angle is distinctly lowered by the method provided according to the invention and the surface is thus hydrophilized.

It is possible according to the invention to produce a glass cylinder for a piston-cylinder arrangement in which the surface of the inside of the cylinder is formed by the glass of the glass cylinder, and wherein the contact angle of this surface with water is less than 15°. Since the surface is formed by the glass itself, the glass cylinder is thus not coated, unlike in known glass syringes.

In principle, it is possible to use all possible kinds of glass, such as soda-lime glass, aluminosilicate glass, borosilicate glass, quartz glass, various glass ceramics and so forth. Borosilicate glasses are particularly suitable.

The effect of the hydrophilization as caused by the gas discharge provided according to the invention can be stabilized by the loading with water. The reaction of the glass surface with water molecules after the effect of the gas discharge can obviously lead to the effect that the reactive sites at the surface react with water and hence are satisfied. As a result, any reaction with other co-reactants can proceed with difficulty at best, if at all. It is the case that the loading may be commenced within 60 minutes after the gas discharge has ended. This loading may also include the filling with the active ingredient formulation.

It is apparent from the studies in J. Abenojar et al., International Journal of Adhesion & Adhesives 44 (2013) 1-8 that a plasma treatment of a glass surface by a plasma flare entails an increase in bridge-forming oxygen relative to non-bridge-forming oxygen. It is assumed that a corresponding effect is also observed in the gas discharge or plasma, UV or ozone treatment caused inside the glass cylinder. In addition, C-containing compounds that have accumulated on the glass surface from the atmosphere are broken up or fragmented, or the bonding to the silanol groups on the glass surface is broken, and then they are transported away via air flow/convection.

In the surface activation of the glass with UV light or ozone, the process is especially as follows: owing to their high energy, the UV photons are capable of breaking chemical bonds in the molecular network of the glass. The opened bonding sites will aim to attain a chemically stable state again as quickly as possible. Possible co-reactants for this purpose are, for example, the oxygen from the atmosphere or ozone, which can especially be formed from the ambient oxygen in the case of incidence of UV. The open bonds are satisfied from the atoms and radicals formed therefrom, forming new compounds at the glass surface. As a result, the surface takes on a higher polar character, which also affects the surface energy and hence the contact angle with respect to water.

In some embodiments, the ratio of bridge-forming oxygen to non-bridge-forming oxygen at the surface of the inside of the cylinder is elevated relative to the value of this ratio in the interior of the glass. In some embodiments, the ratio of oxygen to silicon at the surface of the inside of the cylinder is elevated relative to the value of this ratio in the interior of the glass. This effect too, which brings about an increase in the polar component of the surface energy, is described in the above-cited article.

T. Ishibe et al., "Absorption of nitrogen dioxide and nitric oxide by soda lime", British Journal of Anaesthesia 1995; 75:330-333 further discloses that nitrogen monoxide, NO and nitrogen dioxide, $NO_2$, are absorbed by glass, and the absorption of NO takes place only in the simultaneous presence of $NO_2$. Both substances are generated in a gas discharge in a gas containing nitrogen and oxygen, i.e. especially also in a gas discharge in the presence of air. Therefore, in some embodiments, it is the case that the glass on the inside of the cylinder contains nitrogen oxides or more generally nitrogen compounds at or close to the surface.

Using a glass cylinder as characterized above and producible in accordance with the invention, it is then possible to produce a piston-cylinder arrangement with the glass cylinder, and a piston inserted into the glass cylinder, which is also referred to as gasket, wherein the piston runs directly on the glass of the glass cylinder, wherein at least the running surface of the piston is formed by a plastic, wherein the plastic of the running surface has a greater contact angle with water than the surface of the inner cylinder wall formed by the glass of the glass cylinder. Typically, the difference is sufficiently great that the running surface of the piston can be characterized as hydrophobic and the glass as friction partner as hydrophilic.

More particularly, the contact angles of plastic of the running surface and inner cylinder wall with water may have a differential of at least 60°, such as at least 70°. By virtue of the high differential, it is possible to achieve good sliding properties without needing a lubricant, for instance the silicone oil used otherwise. Exemplary embodiments provided according to the invention can then also be utilized for controlled establishment of a particular defined difference in the contact angles of running surface of the piston and inside of the cylinder, by conducting the gas discharge or plasma or ozone treatment until the contact angle of the glass surface has fallen to such a degree that the defined differential is attained. Moreover, this also achieves a homogeneous contact angle across the longitudinal side of the cylinder.

In general, the method described is usable whenever hydrophilic glass surfaces are to be produced. This is not just restricted to cylindrical shaped bodies, but in some embodiments may also be flat forms which, in some embodiments, are then also shaped, for example by rolling up a thin glass.

It is then possible, with the piston withdrawn, to take a liquid active ingredient formulation up into the piston-cylinder arrangement, which may be in the form of a glass syringe, and store it therein. In this way, correspondingly, a prefilled syringe is provided.

Particularly in the case of complex active ingredients of high molecular weight, such as insulin, vaccines, antibodies, blood products, hormones, cytokines, and generally protein-based active ingredients, in the case of use of silicone to lower the friction between piston and cylinder, there is the risk of agglomeration of the respective active ingredient at the siliconized surface or the formation of dissolved silicone particles in the pharmaceutical product. The same also applies in the case of other organic lubricants. Exemplary embodiments of the glass syringe provided according to the invention, which is especially free of silicone or lubricant, eliminates this problem or at least distinctly reduces the risk of agglomeration. In some embodiments, therefore, a piston-cylinder arrangement is provided in the form of a glass syringe that accommodates a liquid active ingredient formulation containing an active ingredient having a molecular weight of at least 1000 grams/mole.

In general, without restriction to the example shown in FIG. 1, in one aspect of the invention an apparatus 7 for treatment of a glass cylinder 3 for a piston-cylinder arrangement for reduction of the friction of the piston at the inner cylinder wall is provided. The apparatus 7 is configured to generate a corona discharge in the glass cylinder 3. The apparatus 7 comprises a high-frequency generator 13, a high-frequency transformer 14 and an electrode station 15.

The high-frequency generator 13 generates an output signal, the frequency of which may automatically settle in the range of 15-25 kHz according to the resistance and hence optimizes the treatment power. The electrode station 15 of the apparatus 7 comprises at least one electrode 150 and one counterelectrode 151. The electrodes may be specially adapted for each application, or to various forms of glass cylinders 3. The functionalizing corona discharge may be generated with air under atmospheric pressure. The electrode 150 is elongated and inserted in axial direction of the glass cylinder 3. The counterelectrode 151 is tubular and surrounds the glass cylinder 3. This ensures a virtually homogeneous field distribution, such that the surface of the inside 30 that consists of glass 2 is exposed uniformly to the corona discharge. In order to be able to gain a particularly homogeneous effect of the corona discharge, during the corona discharge, it is also possible to conduct a relative movement of glass cylinder 3 and the arrangement of the electrodes 150, 151.

In the example shown, the glass cylinder 3 is the cylinder for a glass syringe 1. For this purpose, the glass cylinder 3 comprises an inner cylinder wall 30 as a sliding surface for a piston 5 which bounds a cylinder interior 31, and a holding element for a syringe needle, typically in the form of a Luer cone 32. Typically, such glass cylinders 3 also have a flange 33 at the piston introduction opening 34. If the electrical discharge is not undertaken under air and/or not under atmospheric pressure, the glass cylinder 3 may also be sealed at this flange 33 in order to at least partly evacuate the interior 31.

Corona discharge is used in an exemplary embodiment provided according to the invention. Apart from gas discharges, such as plasma treatment and specifically corona discharges, there are also other methods of altering the glass 2 at its surface in accordance with the invention. More particularly, these may generally be methods that generate free radicals that then react with the glass 2. For instance, ozone can be generated by a gas discharge in an oxygen-containing gas or else by irradiation with ionizing rays, such as more particularly by UV radiation, for example from the ambient oxygen. In some embodiments, the device 7 comprises a loading device 8, in order to load the inside 30 of the glass cylinder 3 that has been treated by the gas discharge beforehand with water. In some embodiments, a device 10 for enrichment of air with water is provided, in order to provide air with a high moisture level. Using a feed device 10, the air is then introduced into the interior 31 of the glass cylinder. By contrast to what is shown in FIG. 1, the loading device 8 may also comprise a separate loading station. In this embodiment, the glass cylinders are sent successively first to a loading station for treatment of the inside 30 by the gas discharge and then to a loading station for loading with water.

However, it has also been shown that the hydrophilic properties of the glass surface remained stable after the treatment by gas discharge, for instance plasma or corona discharge, even without temporary loading. In some embodiments, therefore, the loading device can also be dispensed with.

Figure 2:
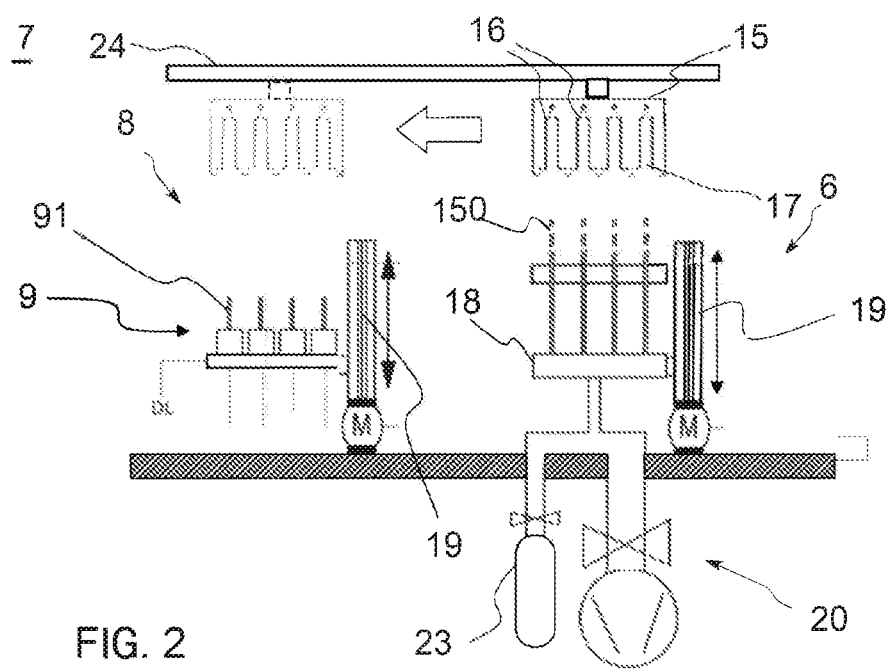
FIG. 2 illustrates another exemplary embodiment of an apparatus provided according to the invention for treating a glass cylinder using a corona discharge or another form of a plasma.

In another exemplary embodiment shown in FIG. 2, it is possible to use an inventive apparatus 7 that constitutes a modification of the arrangement known from WO 2012/097972 A1. The apparatus 7 comprises at least one glass cylinder holder 15 with one or more than one holding chamber 16, these having at least one open end 17 through which a glass cylinder 3 to be treated can be introduced, such that an opening of the glass cylinder 3 points toward the open end of the holding chamber 16. In addition, the apparatus 7 comprises a movable closure element 18 that can be combined with the glass cylinder holder 15 via a lifting apparatus 19, such that, on closure by the lifting apparatus 19 by movement of the closure element 18 onto the glass cylinder holder 15 to give an accommodated glass cylinder 3, there is sealing at an opening of the glass cylinder, such as at the piston introduction opening 34 thereof, with respect to the outside atmospheric pressure. In addition, the apparatus 7 comprises a device 6 for generating a gas discharge, which in this embodiment is isolated from the outside atmospheric pressure, especially a corona discharge or another form of a plasma with two electrodes, by which an electric or electromagnetic field can be generated in the interior of an accommodated and sealed glass cylinder 3. Similarly to the case of the example shown in FIG. 1, one of the electrodes 150 here is an internal electrode which is introduced axially into the glass cylinder 3 through the piston introduction opening 34. The glass cylinder holder 15 may then form or contain the counterelectrode.

The device 6 for generating a gas discharge, especially a corona discharge or plasma, for example in an $O_2$, $O_2/Ar$ or $O_2/N_2$ atmosphere, comprises a device 20 for evacuating the interior 31 via a gastight connection at the closure element 18 and at least one treatment tool that can be combined with the open end 17 of the glass cylinder holder 15 for at least one component step of the surface treatment of the vessels. In some embodiments, the evacuation is not conducted completely, or evacuation is followed by supply of a process gas from a process gas vessel 23 a desired process gas, such that the gas pressure in the gas discharge is at least 100 millibars.

In some embodiments, the evacuation is conducted into the low-pressure range, such that the gas pressure during the surface treatment is at most 10 mbar, but also at least 0.3 mbar.

The apparatus 7 also has a loading device 8 spatially separate from the device 6 for generating the gas discharge, especially a corona discharge or another form of a plasma, with which a particular amount of water can be applied to the inner glass cylinder wall 30. A transport device 24 transports the glass cylinder holder with the glass cylinders accommodated therein, by transport device 24, from the device 6 for generating a gas discharge, especially a corona discharge or another form of plasma, to an optional loading device 8. For the loading device 8 too, as shown, a lifting apparatus 19 may be provided in order to combine the loading tool with the glass cylinder holder 15 and the glass cylinders 3 accommodated therein. The loading device 8, as in the embodiment of FIG. 1, comprises a device 9 for enrichment of air with water. The enriched air is introduced into the glass cylinders via gas probes 91.

The device 6 may be configured either to generate a corona discharge or another form of a plasma, for example a glow discharge.

The method step of treatment by the gas discharge or the plasma or by ozone and the associated activation of the glass on the inside 30 may also be repeated here as often as desired in order, if appropriate, to achieve an improvement in the result. In some embodiments, a treatment with water is conducted, in which case the activating and subsequent loading, which may be in the form of cleaned air enriched with water (WFI), is conducted at least twice in succession. It is additionally also conceivable to conduct the method steps, in particular applications, independently of one another as a one-step process.

The gas discharge may be monitored and optionally controlled with regard to power and duration of treatment. The sliding coefficient on the surface can be controlled via the power of the source and the residence time in this method step on the particular vessel. It is thus possible to adjust the property of the surface in a controlled manner even to the properties of the gasket to be inserted later. There is no risk of layer detachment or particle formation in the treatment provided according to the invention, which reduces interaction with the pharmaceutical and the contamination risk to the patient to a minimum.

A further advantage of exemplary embodiments provided according to the invention is the universal usability of the method and of the apparatus for a wide variety of different packaging materials. The method provided according to the invention may also be used additionally as an inexpensive and safe alternative in place of a standard or baked siliconization. The sliding surface in the form of a glass surface is cleaned and activated in a first step by high-frequency high-voltage discharge. A second process step may follow, in which the first sliding surface is contacted or loaded with water, such as WFI water in the form of steam. On loading with enriched air, the amount of water is sufficiently low that an additional drying step can be dispensed with. The contacting with water can alternatively be effected by the filling with an active ingredient formulation.

As well as a low contact angle of the glass 2 with water which is achievable in accordance with the invention, homogeneous development of the surface energy on the inner cylinder wall 30 is also advantageous. If there is a change in the surface energy, there will also be variation in the friction resistance with respect to the friction partner. This can even go to the extent that the piston is blocked at a given expended propulsion force. Even a merely varying resistance on movement of the piston 5 may be very disadvantageous, for instance when this makes it difficult to exactly dose medicaments with a glass syringe 1 as shown, for example, in FIG. 4. In some embodiments, it is therefore the case that the gas discharge or plasma, UV or ozone treatment does not just lower the contact angle with water, but that the size of the contact angle of the glass 2 with water in the axial direction of the glass cylinder also has a variation which is lowered by the gas discharge or plasma, UV or ozone treatment. It is generally a feature of a glass cylinder 3 provided according to the invention that the variation of the contact angle in longitudinal direction from end to end of the glass cylinder 3 is less than 5°.

Figure 3:
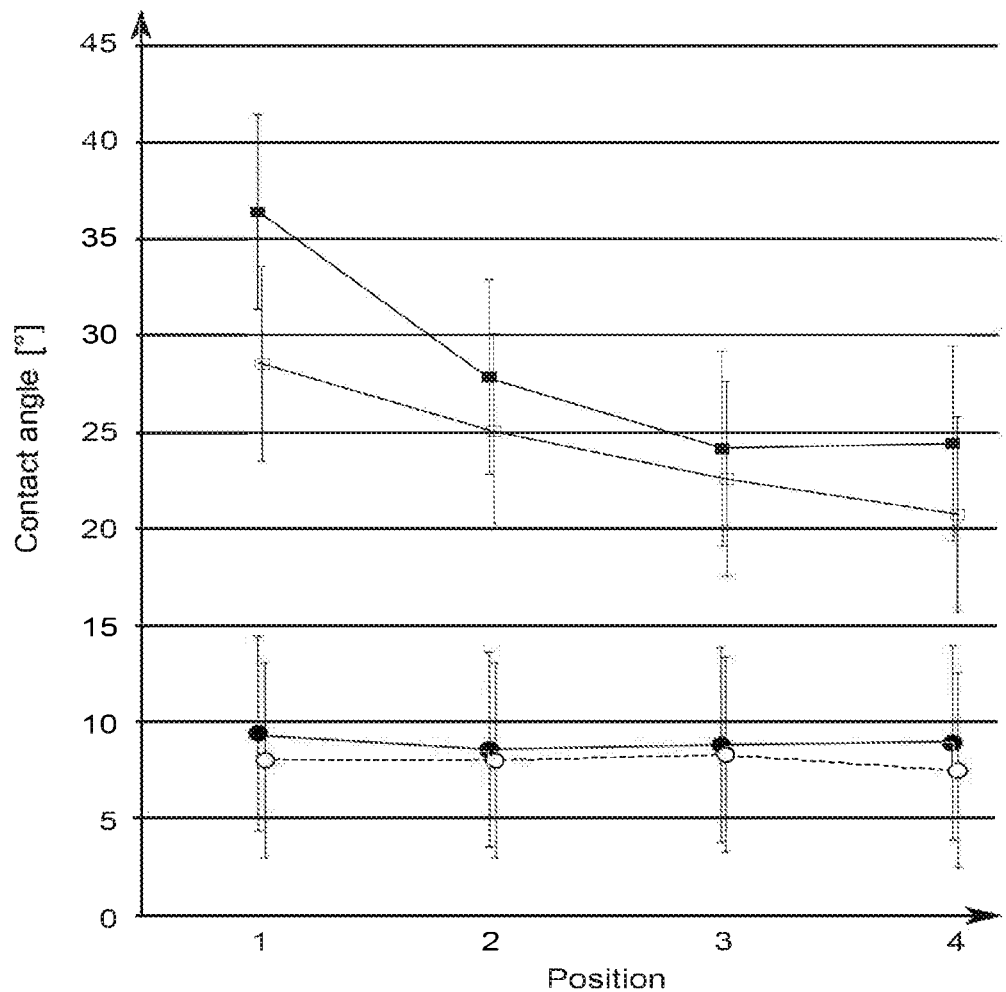
FIG. 3 is a diagram with measurements of the contact angle at various longitudinal positions on an untreated glass syringe and a syringe treated by a gas discharge.

One example in this regard is shown by the diagram in FIG. 3. In this diagram, the measurements of the contact angle of the class 2 with water are entered at four longitudinal positions in an untreated glass syringe 1 and in a glass syringe 1 treated by a gas discharge. Position 1 is at the piston introduction opening 34 of the glass syringe 1, as shown, for example, in FIG. 4. The further positions 2, 3 and 4 are respectively spaced apart from position 1 by 1.3 cm, 2.3 cm, 3.3 cm, and 4.3 cm.

The measurements shown as squares were measured on an untreated glass syringe 1. Circles show the measurements that were treated by a gas discharge on the inside in accordance with the invention. Filled symbols represent the measurements at the start of the experiment. After this first measurement, the glass syringes 1 were stored in a protective gas atmosphere for four days, then a further measurement was conducted. These measurements on the untreated syringe and on the syringe 1 provided according to the invention are each shown by open symbols, i.e. open squares (untreated syringe) and open circles (treated syringe).

The measurements of contact angle were undertaken by the sessile drop method to DIN 55660 with the following slight departures from the standard: the measurements took place at room temperature 22° C. and 37% relative air humidity (the standard is 23° C., 50% rh). Owing to the curvature of the surface, droplets having a volume of 1.5 microliters were used rather than the stipulated 2 microliters.

As apparent from the measurements, the inventive treatment with a gas discharge leads to lowering of the contact angle with water to below 10°. It is also particularly advantageous that the effect is maintained over the storage period of 4 days. By contrast with the untreated syringe, the variation in the contact angle in the longitudinal direction of the glass cylinder 3 is very small. In the case of the untreated syringe, the contact angle is at its greatest at the piston introduction opening 34 and drops toward the other end, i.e. toward the Luer cone. The difference both in the case of the syringe as supplied and in the case of the syringe stored for 4 days is about 15°. Thus, the variation in the angle is already greater than the contact angle of the glass cylinder 3 treated in accordance with the invention. This variation is less than 5° in the example shown. Variation of less than 3° is also possible in general, as shown by the example.

The low contact angle of the inventive example has already been achieved in a single treatment. In general, it is also possible in some embodiments provided according to the invention that the steps of causing a gas discharge and loading with water are repeated at least once.

Figure 4:
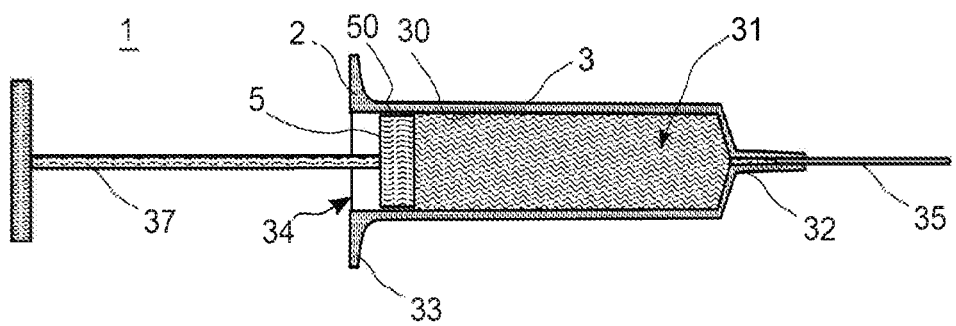
FIG. 4 illustrates a filled glass syringe.

FIG. 4 shows an exemplary application of a piston-cylinder arrangement 4 in the form of a glass syringe 1 that is provided in accordance with the invention. More particularly, the glass syringe 1 may be provided as a prefilled syringe, with a liquid active ingredient formulation 11 accommodated in the interior 31 of the glass cylinder 3 with the piston 5 withdrawn. The glass syringe 1 may also already have been equipped with a cannula 35 secured to the Luer cone. For example, the cannula 35 may be adhesive-bonded. The cannula 35 can also be secured, for example, by a method as described in WO 2012/034648 A1. This involves fusing the cannula into the Luer cone, such that plastics are dispensed with here too by avoiding an adhesive bond. The disclosure of the document cited is also incorporated fully into the subject matter of the present application with regard to the method of radiation-assisted heating of the glass and of fusing-in of the cannula.

What is unusual about the glass syringe 1 provided according to the invention is that the running surface 50 of the piston 5 runs directly on the glass 2 of the glass cylinder 3, i.e. no lubricant layer, especially none comprising silicone, is present. The liquid active ingredient formulation, owing to the low contact angle of the glass 2 treated, forms a liquid film on the surface on which the running surface 50 slides. The running surface 50 of the piston 5 may be a plastic, especially a plastic that has a greater contact angle to water than the glass surface treated in accordance with the invention. The contact angles of plastic of the running surface 50 and inner cylinder wall 30 with water have a differential of at least 60°, such as at least 70°. In some embodiments, the plastic of the running surface is chosen such that the contact angle thereof with water is at least 70°, such as at least 80°.

As stated, for a given material of the running surface 50, it is also possible to establish a particular differential in contact angle in a controlled manner by lowering the contact angle of the glass 2 via the duration and/or intensity of the gas discharge or plasma, UV or ozone treatment to such an extent that the desired differential is attained.

The running surface 50 may be in one-piece form with the remaining portion of the piston 5 and of the plunger 33. If appropriate, it is also possible to use a different plastic for the running surface, for example in that a gasket or piston 5 in which at least the surface of the seal has a halogenated polymer, such as a fluoropolymer. Gaskets of this kind, which are desirable, for example, for particular active ingredients to be administered, are found to be particularly advantageous in conjunction with the syringe provided according to the invention and relation to the sliding and sealing properties.

Since there is no risk of coagulation of comparatively complex active ingredients under the influence of silicone, as exists in the case of silicone-containing sliding films, exemplary embodiments provided according to the invention are also particularly suitable for such active ingredients. More particularly, this advantage exists in the case of active ingredients having molecular weight of 1000 grams per mole.

Figure 5:
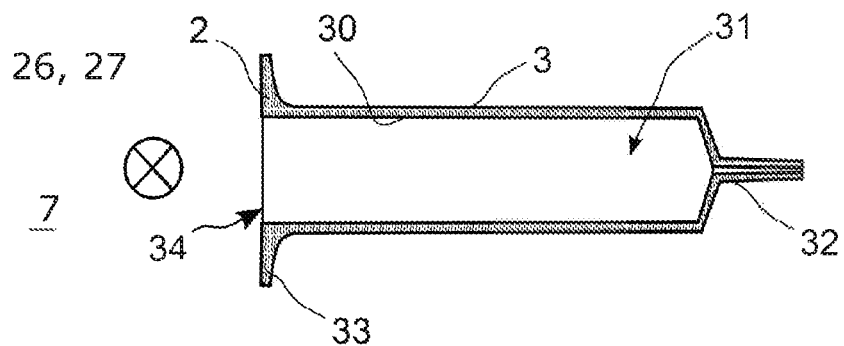
FIG. 5 illustrates an exemplary embodiment of an apparatus provided according to the invention for treating a glass cylinder using a radiation source for ionizing radiation.

It will be apparent to the person skilled in the art that the invention is not restricted to the specific examples shown in the figures, but can instead be varied in various ways. For instance, in the example of FIG. 4, a syringe with a fixed cannula 35 is shown. The cannula 35 may alternatively only be attached on use. Carpules are also considered to be syringes within the scope of the invention. FIG. 5 shows parts of an apparatus 7 for treatment of a glass cylinder 3 by a radiation source 26 for ionizing radiation, especially a UV source 27. The apparatus 7 in the working example comprises a UV source 27, for example in the form of a low-pressure UV source with a tube having the wavelength of 185/254 nanometers. The UV treatment of the glass cylinder 3, especially the glass syringe 1, generates ozone in the interior of the glass cylinder, which is then exposed to the inner wall of the glass cylinder 3 for a desired period of time. The treatment may be arranged within or outside the surfaces of the glass 2. The method of activation of the surface initiated via ozone may also be repeated any number of times in order to obtain an improvement in the result. The sliding coefficient on the surface can be adjusted in a controlled manner via the residence time in this method step on the respective vessel, the glass 2, the gasket or piston 5 and the other article. There is no risk of layer detachment or particle formation in the treatment provided according to the invention, which reduces interaction with the pharmaceutical and the risk of contamination to the patient to a minimum.

A further advantage of exemplary embodiments provided according to the invention is the universal usability of the method and of the apparatus for a wide variety of different packaging materials. The method provided according to the invention may also additionally be used as an inexpensive and safe alternative in place of a standard or baked siliconization.

Ozone can also be generated by ionization of oxygenous gas, for example by irradiation in a reaction space separate from the piston 5, and the ozone-containing gas can then be guided out of the reaction space into the piston 5.

As in the case of the embodiment with the treatment by a gas discharge, the hydrophilization by the action of ozone can be stabilized by an aftertreatment with water, for instance by water vapor.

The methods provided according to the invention allow surface treatment which is stable over a long period, including transport and storage, for up to a few years.

There follows a description of three inventive treatments of the inner cylinder walls 30 of glass syringes 1.

In working example 1, there is a surface modification of the inner cylinder wall 30 of a glass syringe 1 by corona discharge in the air. For this purpose, the glass syringe 1, in an apparatus 7 according to FIG. 1, is mounted in the counterelectrode 151 made of brass and the electrode 150 of aluminum is inserted into the glass cylinder 3. The corona discharge is effected at an effective voltage of 3 kV and a frequency of 15 kHz. The duration can be varied and in this example is 1 second (0.1 to 30 seconds were tested).

In working example 2, there is a surface modification of the inner cylinder wall 30 of a glass syringe 1 by UV/ozone. For this purpose, the glass syringe 1, in an apparatus 7 according to FIG. 5, is exposed to the UV radiation from the UV source 26 and ozone for a period of time between 1 second and 10 minutes. In the specific example, the treatment time was 15 seconds.

In working example 3, there is a surface modification of the inner cylinder wall 30 of a glass syringe 1 by oxygen/plasma. For this purpose, the glass syringe 1 is positioned in an apparatus 7 according to FIG. 2, wherein the electrode 150 is arranged in the cavity of the glass cylinder 3 and the glass syringe 1 is sealed. The reactive gas is introduced through the electrode 150 itself. The oxygen pressure is adjusted to 0.3 mbar and the plasma is ignited for 10 seconds at a frequency of 60 kHz and a current of 10 mA.

Figure 6:
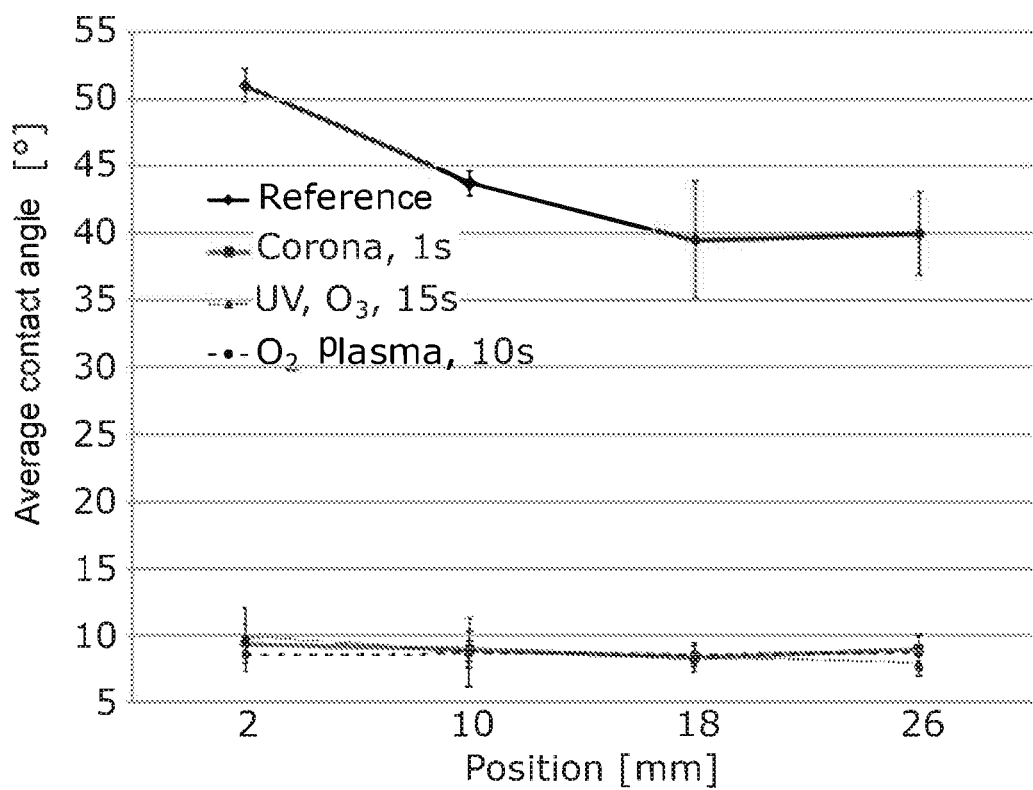
FIG. 6 is a diagram with measurements of the contact angle at various longitudinal positions on an untreated glass syringe (reference) and of syringes provided in accordance with the invention.

In FIG. 6, the measurements of the contact angle are entered at four different longitudinal positions on an untreated glass syringe (reference), a glass syringe 1 that has been treated by corona discharge in air for 1 second (according to working example 1), a glass syringe 1 that has been treated by UV/ozone for 15 seconds (according to working example 2), and a glass syringe 1 that has been treated by oxygen/argon for 10 seconds (according to working example 3). The distance here is reported from the flange at the piston introduction opening 34 of the respective glass syringe 1. The first position is 2 mm away from the flange 33. The further positions are reported at a distance of 10 mm, 18 mm and 26 mm from the flange 33 at the piston introduction opening 34. The measurements of the contact angles were undertaken by the method described above for FIG. 3.

As apparent in FIG. 6, the contact angle of the inner cylinder wall 30 of the glass syringe 1 that has been treated by corona discharge is less than 10°.

The contact angle of the inner cylinder wall 30 of the glass syringe 1 that has been treated by UV/ozone, according to FIG. 6, has likewise dropped to a value of less than 10°, homogeneously over the length of the syringe.

As shown in FIG. 6, the contact angle of the inner cylinder wall 30 of the glass syringe 1 treated by oxygen/plasma, homogeneously over the length of the syringe, is also less than 10°.

Figure 7:
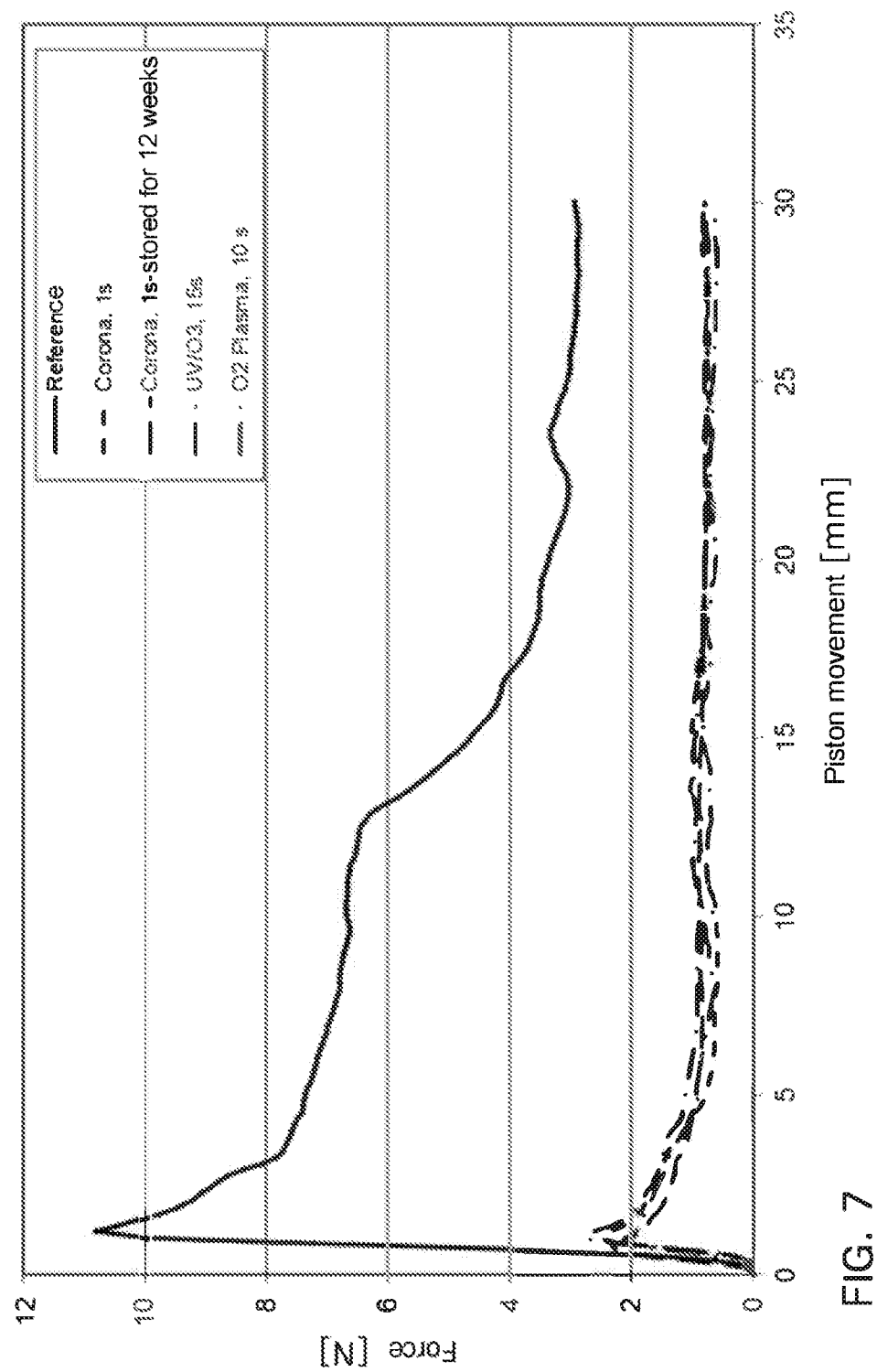
FIG. 7 is a diagram with measurements of stick-slip friction forces for an untreated glass syringe (reference) and for syringes provided in accordance with the invention.

FIG. 7 is a diagram with measurements of the stick-slip friction forces for an untreated glass syringe (reference) and for glass syringes 1 treated in accordance with the invention. As apparent in FIG. 7, the stick-slip friction force measured on glass syringes 1 that have been treated by corona discharge in air for 1 second (according to working example 1) is significantly less than for the untreated reference glass syringe, which is attributable to a homogeneous, superhydrophilic surface.

After the corona discharge, the glass syringes were stored under room temperature conditions for 12 weeks and stick-slip friction was measured again. The values are comparable with those of freshly treated syringes as shown in FIG. 7.

The stick-slip friction force of the glass syringes 1 that have been treated by UV/ozone for 15 seconds (according to working example 2), according to FIG. 7, is likewise significantly lower than for the untreated reference glass syringe.

The same is true of the glass syringes 1 that have been treated by oxygen/argon for 10 seconds (according to working example 3), as shown in FIG. 7.

Figure 8:
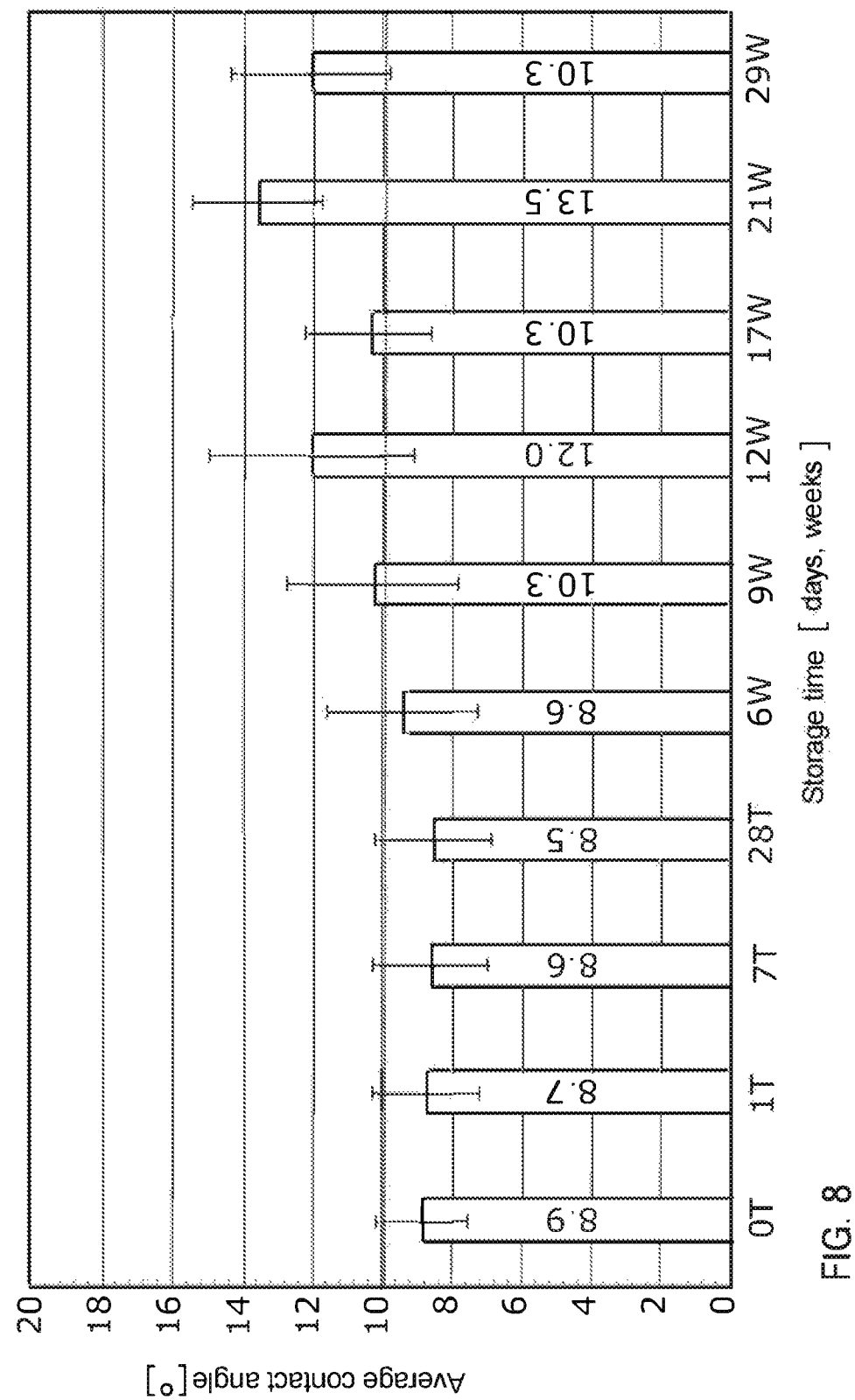
FIG. 8 is a bar diagram with measurements of the contact angle for glass syringes treated by corona discharge over various storage times.

In order to test the long-term stability of the treatment, glass syringes 1 were treated by corona discharge (according to working example 1) and then stored at room temperature, and the contact angle was measured after time intervals of 1 day, 7 days, 28 days, 6 weeks, 9 weeks, 12 weeks, 17 weeks, 21 weeks and 29 weeks of storage time. FIG. 8 is a bar diagram with the average values of the measurements of the contact angle for 10 glass syringes treated by corona discharge per group at 4 positions each over the storage times mentioned.

As apparent from FIG. 8, the contact angle remains stable over the storage time of up to 29 weeks. This is significantly longer than described in literature (in S. Takeda, J. Non Cryst Solids, (249) 199, 41-46), in which, after about 8 days, the contact angle of various glass types has risen again to a constant value.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

| List of reference numerals | |
| --- | --- |
| 1 | glass syringe |
| 2 | glass |
| 3 | glass cylinder |
| 4 | piston-cylinder arrangement |
| 5 | piston |
| 6 | device for generating a gas discharge |
| 7 | apparatus for treating a glass cylinder 3 |
| 8 | loading device |
| 9 | device for enriching air with water |
| 10 | feed device |
| 11 | active ingredient formulation |
| 13 | high-frequency generator |
| 14 | high-frequency transformer |
| 15 | glass cylinder holder |
| 16 | holding chamber |
| 17 | open end of 16 |
| 18 | closure element |
| 19 | lifting apparatus |
| 20 | device for evacuating 31 |
| 23 | process gas vessel |
| 24 | transport device |
| 26 | radiation source for ionizing radiation |
| 27 | UV source |
| 30 | inner cylinder wall |
| 31 | interior of 3 |
| 32 | Luer cone |
| 33 | flange |
| 34 | piston introduction opening |
| 35 | cannula |
| 37 | plunger |
| 50 | running surface of 5 |
| 91 | gas probes |
| 150 | electrode |
| 151 | counterelectrode |

What is claimed is:

1. A method of treating a glass cylinder for a piston-cylinder arrangement for reducing the friction of a piston on an inner cylinder wall of the glass cylinder, the method comprising:
   elevating surface energy of glass of an interior bounded by the inner cylinder wall and hence lowering a contact angle of the glass with water, wherein the contact angle is lowered by:

a gas discharge that acts on the glass at the inner cylinder wall and is generated by an electric or electromagnetic field; or the action of ozone on the glass surface;

contacting the glass with the lowered contact angle with water vapor to form a water film on the glass; and placing a piston in the interior such that the formed water film is disposed between the piston and the glass.

2. The method of claim 1, wherein at least one of the steps of causing a gas discharge, causing the action of ozone, or contacting with water are repeated at least once.

3. The method of claim 1, further comprising filling the interior with an aqueous active ingredient formulation, wherein the formed water film is present on the glass prior to filling.

4. The method of claim 1, wherein the contact angle is lowered by a gas discharge and the gas discharge is effected in an oxygen-containing gas.

5. The method of claim 1, wherein the contact angle is lowered by ozone and the ozone is generated by at least one of the processes of:

a gas discharge in an oxygen-containing gas;

an irradiation with ionizing rays; or a UV irradiation.

6. The method of claim 1, wherein the contact angle is lowered by a gas discharge and the gas discharge is effected at a gas pressure of at least 100 millibars or at a gas pressure of at most 10 millibars.

7. The method of claim 1, wherein the contact angle is lowered by a gas discharge and the gas discharge comprises a corona discharge or a plasma treatment.

8. The method of claim 1, wherein the contact angle of the glass with water in an axial direction of the glass cylinder has a variation, the magnitude of which is lowered by the gas discharge or by the action of ozone.

9. The method of claim 1, further comprising defining a differential of the contact angle of a running surface of the piston and the inside of the cylinder, wherein the gas discharge or the action of ozone is conducted until the contact angle of the glass has fallen to such a degree that the defined differential is attained.

10. The method of claim 1, further comprising placing a piston in the interior, wherein a differential is formed between a contact angle of plastic of a running surface of the piston and the glass with the lowered contact angle, the differential being at least 60°.

11. The method of claim 1, wherein the inner cylinder wall is free of at least one of silicone or a lubricant.

12. The method of claim 1, wherein the lowered contact angle is stable over a storage time of up to 29 weeks.

13. The method of claim 12, wherein the storage time is at least 2 weeks.

14. The method of claim 1, wherein the lowered contact angle is a contact angle with water of less than 15°.

15. The method of claim 1, wherein a variation in the contact angle of the glass with water in a longitudinal direction from one end of the glass cylinder to the other is less than 5°.

16. A piston-cylinder arrangement, comprising:

a glass cylinder comprising an interior bounded by an inner cylinder wall, wherein a surface of the interior of the cylinder is formed by a glass of the glass cylinder and a contact angle of the surface with water is less than 15° so the surface is hydrophilic; and a piston inserted into the glass cylinder that runs directly on a water film formed on the glass of the glass cylinder from water vapor so the formed water film is disposed between the piston and the glass.

17. A piston-cylinder arrangement comprising:

a glass cylinder comprising:

an interior bounded by an inner cylinder wall, wherein a surface of the interior of the cylinder is formed by a glass of the glass cylinder and a contact angle of the surface with water is less than 15° so the surface is hydrophilic; and a piston inserted into the glass cylinder that runs on a water film formed on the glass of the glass cylinder from water vapor, wherein at least a running surface of the piston is formed by a plastic that has a greater contact angle with water than the surface of the inner cylinder wall formed by the glass of the glass cylinder.

18. The method of claim 1, wherein the contact angle is lowered by a gas discharge and the gas discharge is below atmospheric pressure.

* * * * *